(12) United States Patent
Ito et al.

(10) Patent No.: US 12,329,847 B2
(45) Date of Patent: Jun. 17, 2025

(54) COSMETIC COMPOSITION

(71) Applicant: TAIYO KAGAKU CO., LTD., Yokkaichi (JP)

(72) Inventors: Satoko Ito, Yokkaichi (JP); Yuichi Sakanishi, Yokkaichi (JP); Tomonori Higuchi, Yokkaichi (JP)

(73) Assignee: TAIYO KAGAKU CO., LTD., Yokkaichi (JP)

( * ) Notice: Subject to any disclaimer, the term of this patent is extended or adjusted under 35 U.S.C. 154(b) by 0 days.

(21) Appl. No.: 18/870,764

(22) PCT Filed: Apr. 28, 2023

(86) PCT No.: PCT/JP2023/016814
§ 371 (c)(1),
(2) Date: Dec. 2, 2024

(87) PCT Pub. No.: WO2023/243243
PCT Pub. Date: Dec. 21, 2023

(65) Prior Publication Data
US 2025/0170046 A1    May 29, 2025

(30) Foreign Application Priority Data

Jun. 13, 2022 (JP) ................. 2022-095275

(51) Int. Cl.
| | |
|---|---|
| *A61K 8/04* | (2006.01) |
| *A61K 8/02* | (2006.01) |
| *A61K 8/31* | (2006.01) |
| *A61K 8/37* | (2006.01) |
| *A61K 8/39* | (2006.01) |
| *A61K 8/86* | (2006.01) |
| *A61Q 1/00* | (2006.01) |
| *A61Q 1/14* | (2006.01) |
| *A61Q 19/00* | (2006.01) |

(52) U.S. Cl.
CPC .............. *A61K 8/86* (2013.01); *A61K 8/0291* (2013.01); *A61Q 19/00* (2013.01); *A61K 2800/10* (2013.01)

(58) Field of Classification Search
None
See application file for complete search history.

(56) References Cited

U.S. PATENT DOCUMENTS

2021/0315787 A1 * 10/2021 Matsumoto .............. A61K 8/37

FOREIGN PATENT DOCUMENTS

| | | |
|---|---|---|
| JP | 2003-327506 A | 11/2003 |
| JP | 2004-35420 A | 2/2004 |
| JP | 2004-359568 A | 12/2004 |
| JP | 2005-213236 A | 8/2005 |
| JP | 2020-40918 A | 3/2020 |
| JP | 2022-83925 A | 6/2022 |
| JP | 2023-55499 A | 4/2023 |
| WO | WO 2020/116011 A1 | 6/2020 |

OTHER PUBLICATIONS

Decision of Grant for Japanese Application No. 2023-552306, dated Jan. 11, 2024.
International Search Report, issued in PCT/JP2023/016814, PCT/ISA/210, dated Jul. 18, 2023.
Notice of Grounds for Rejection for Japanese Application No. 2023-552306, dated Oct. 24, 2023.

* cited by examiner

*Primary Examiner* — Brian Gulledge
(74) *Attorney, Agent, or Firm* — Birch, Stewart, Kolasch & Birch, LLP

(57) ABSTRACT

A cosmetic composition containing the following components (A) to (C), wherein the mixed HLB of components (B) and (C) is from 11.1 to 15.0:
 component (A): oil agent;
 component (B): one or more kinds selected from the group consisting of a polyglycerol fatty acid ester having HLB of less than 13.5 consisting of a polyglycerol in which primary hydroxyls among all hydroxyls are 50% or more and which has an average degree of polymerization of from 6 to 14 and a fatty acid having the number of carbon atoms of 12 or more; and
 component (C): one or more kinds selected from the group consisting of a polyglycerol fatty acid ester having HLB of 13.5 or more and a polyglycerol monoalkyl ether having HLB of 12 or more.

The cosmetic composition of the present invention can be suitably used in cosmetics.

13 Claims, 1 Drawing Sheet

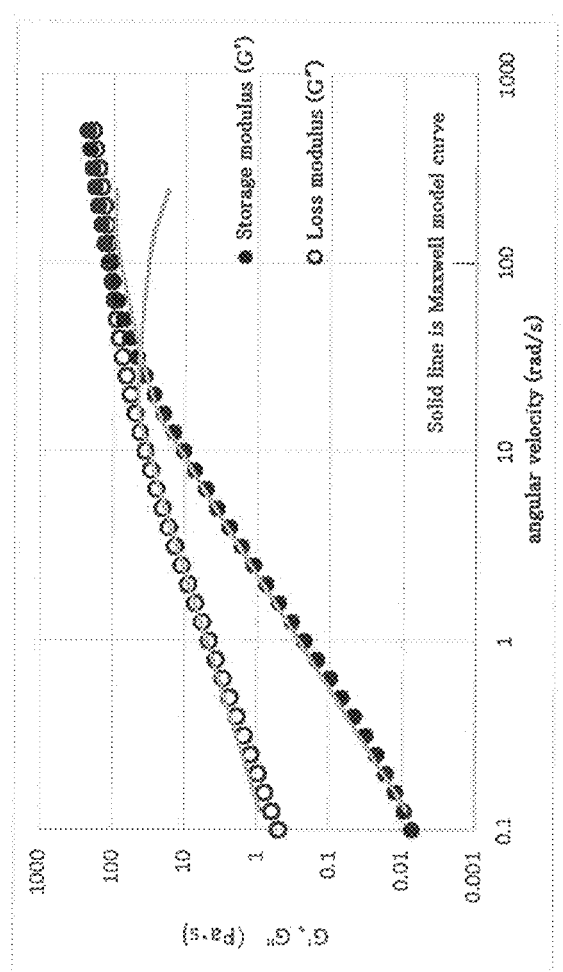

COSMETIC COMPOSITION

TECHNICAL FIELD

The present invention relates to a cosmetic composition and cosmetics containing the composition.

BACKGROUND ART

Recently, since water-proof type makeup products have been popularized, a cleansing agent with high makeup-removing effects is desired. On the other hand, various types of makeup-removing cosmetics such as cream, emulsion, gel and lotion have been sold, and among them oily liquid type cleansing oil utilizes dissolution action of makeup products into oil, so that the oily liquid type cleansing oil has excellent makeup-removing effects. For example, Patent Publication 1 discloses an oily liquid skin cleansing composition characterized by containing one or two or more kinds selected from (A) ester oil, (B) nonionic surfactant having HLB value of 8 or more and less than 12, and (C) polyglyceryl lauryl ether, polyglyceryl dicaprate, polyglyceryl myristate, polyglyceryl tricaprylate and polyglyceryl diisostearate having HLB value of 12 or more, as an oily liquid skin cleansing composition suppressing the stretching feeling of the skin after using the composition, while having excellent removing effects of makeup cosmetics such as rouge, foundation, eye shadow and mascara, and having excellent water resistance in which the makeup removing effects are not decreased even if the composition is used with wet hands.

PRIOR ART REFERENCES

Patent Publications

Patent Publication 1: Japanese Patent Laid-Open No. 2020-40918

SUMMARY OF THE INVENTION

Problems to be Solved by the Invention

However, it was found that the oily liquid skin cleansing composition disclosed in Patent Publication 1 had low viscosity and might have some disadvantages in usability. The ability to remove makeup is largely associated with the properties of the composition itself, in addition to usability thereof. In other words, the composition has to be applied and spread to the portion of interest during cleansing action to make the composition compatible with the makeup. At this time, if the composition disadvantageously drips off, the composition cannot be applied and spread to the portion of interest, even if the composition has high makeup removing effects. In addition, the oily liquid skin cleansing composition disclosed in Patent Publication 1 cannot sufficiently satisfy compatibility with makeup, and needs further improvements.

The present invention relates to providing a cosmetic composition having excellent washout property, having appropriate viscosity in the case where the composition is made as oily cosmetics, and having excellent usability such as good compatibility with makeup, as well as cosmetics containing the composition.

Means to Solve the Problems

The present invention relates to the following [1] to [2]:
[1] A cosmetic composition containing the following components (A) to (C), wherein the mixed HLB of components (B) and (C) is from 11.1 to 15.0:
component (A): oil agent;
component (B): one or more kinds selected from the group consisting of polyglycerol fatty acid ester having HLB of less than 13.5 consisting of a polyglycerol in which primary hydroxyls among all hydroxyls are 50% or more and which has an average degree of polymerization of from 6 to 14 and a fatty acid having the number of carbon atoms of 12 or more; and component (C): one or more kinds selected from the group consisting of a polyglycerol fatty acid ester having HLB of 13.5 or more and a polyglycerol monoalkyl ether having HLB of 12 or more.
[2] Cosmetics containing the cosmetic composition as defined in [1].

Effects of the Invention

According to the present invention, the cosmetic composition having excellent washout property, having appropriate viscosity in the case where the composition is made as oily cosmetics, and having excellent usability such as good compatibility with makeup, as well as cosmetics containing the composition can be provided.

BRIEF DESCRIPTION OF THE DRAWINGS

FIG. 1 shows measurement results of the viscoelasticity for the cosmetic composition of Example 1.

MODES FOR CARRYING OUT THE INVENTION

As a result of intensively studying the above problems, the inventors newly found that a combination use of a combination of the specified polyglycerol fatty acid ester or polyglycerol monoalkyl ether with an oil agent can surprisingly obtain a cosmetic composition having excellent washout property and having appropriate viscosity in the case where the composition is made as oily cosmetics, and having excellent usability such as good compatibility with makeup. Although the reasons why the present invention exhibits such excellent effects are unclear, Example 1 described below confirms that a reverse wormlike micelle which is one of the self-organized body of a surfactant was formed, and it is assumed that the reverse wormlike micelle contributes to the solution of the problems of the present invention. In other words, since the reverse wormlike micelles wind around each other in an oil phase to form a mesh structure, the reverse wormlike micelles can provide to a solution with appropriate viscoelasticity. For example, it is considered that in oily cleansing cosmetics having a reverse wormlike micelle structure, the winding of the reverse wormlike micelles is loosen by a shearing force provided by application and spread during the cleansing, the cosmetics change into oil form and result in feeling likely to be compatible with makeup, while the parts not given a shearing force have viscoelasticity and can be used without dripping off, so that the cosmetics have excellent usability.

In addition, it is generally known that the particle size of O/W emulsion which is caused during washout correlates to a refreshing feeling, but it has been known that the conventional reverse wormlike micelle solution became W/O emulsion by addition of water. On the other hand, it was found that when water is added to the cosmetic composition having the reverse wormlike micelle structure of Example 1 described below, the cosmetic composition becomes O/W emulsion which is unprecedented in the conventional reverse wormlike micelle solution, and the emulsion has the particle size in submicron order, so that the composition has also excellent washout property.

The cosmetic composition of the present invention contains the following components (A) to (C).

The component (A) is an oil agent. The oil agent includes hydrocarbon oil, ester oil, triglyceride, acylglycerol, ether oil, animal and plant oil, silicone oil and the like, and preferably hydrocarbon oil, ester oil, and triglyceride.

The hydrocarbon oil includes hydrogenated polyisobutene, liquid paraffin (mineral oil), light liquid isoparaffin, squalane, undecane, tridecane, isododecane, liquid isoparaffin, hydrogenated polydecene, olefin oligomer, and the like.

The ester oil includes diethylhexyl adipate, avocado oil fatty acid ethyl, alkyl benzoate (C12-C15), isopropyl isostearate, octyldodecyl isostearate, isostearyl isostearate, cholesteryl isostearate, isotridecyl isononanoate, isononyl isononanoate, isodecyl isononanoate, cetyl ethylhexanoate, octyldodecyl erucate, octyldodecyl erucate, isostearyl ethylhexanoate, olive oil fatty acid decyl, olive oil fatty acid octyldodecyl, oleyl oleate, octyldodecyl oleate, decyl oleate, propylheptyl caprylate, caprylyl caprylate/caprate, cocoaprylate/caprate, diethylhexyl succinate, neopentylglycol diisostearate, propyleneglycol dicaprylate, neopentylglycol dicaprate, neopentylglycol diethylhexanoate, dicaprylyl carbonate, pentaerythrityl tetraethylhexanoate, decaglyceryl decaisostearate, octyldodecyl lactate, hexyldecyl neodecanoate, isostearyl palmitate, isopropyl palmitate, ethylhexyl palmitate, isotridecyl myristate, isocetyl myristate, isostearyl myristate, isopropyl myristate, octyldodecyl myristate, isostearyl laurate, lanolin fatty acid isopropyl, hexyl laurate, diisostearyl malate, hexyldecyl stearate, ethylhexyl stearate, ethylhexyl isostearate, decyl isostearate, hexyldecyl isostearate, and the like.

The triglyceride includes triethylhexanoin, glyceryl tricaprylate, glyceryl triisostearate, and the like.

The acylglycerol includes (caprylic/capric) glycerides, glyceryl tricaprylate/caprate, glyceryl diisostearate, and the like.

The ether oil includes dicaprylyl ether, dicaprylyl carbonate, and the like.

The animal and plant oil includes avocado oil, almond oil, olive oil, wheat germ oil, rice germ oil, rice bran oil, safflower oil, soybean oil, corn oil, rapeseed oil, palm oil, palm kernel oil, castor oil, sunflower oil, jojoba oil, macadamia nut oil, coconut oil, and the like.

The silicone oil includes dimethicone, phenyl trimethicone, cyclomethicone, cyclopentasiloxane, diphenylsiloxy phenyl trimethicone, and the like.

The content of component (A) in the cosmetic composition of the present invention is, from the viewpoint of washout property and usability, preferably from 60 to 92% by mass, more preferably from 66 to 88% by mass, and further preferably from 72 to 84% by mass. The content in the case where two or more kinds of the components (A) are used refers to the total amount thereof.

From the viewpoint of increasing viscosity of the cosmetic composition, it is preferable that oil agent having weight average molecular weight of 380 or more is formulated as component (A), more preferably the weight average molecular weight is from 390 to 420, and further preferably the weight average molecular weight is from 421 to 520. As the hydrocarbon oil and ester oil having weight average molecular weight of 380 or more, for example, squalane, liquid isoparaffin, hydrogenated polydecene, mineral oil, olefin oligomer, isocetyl myristate, octyldodecyl myristate, hexyldecyl stearate, ethylhexyl stearate, ethylhexyl isostearate, decyl isostearate, hexyldecyl isostearate, isostearyl isostearate, and the like can be contained.

The content of the oil agent having weight average molecular weight of 380 or more in the component (A) can be adjusted between 5 and 100% by mass depending upon desired viscosity, and from the viewpoint of increasing viscosity of the cosmetic composition, the content is preferably 8% by mass or more, and more preferably 30% by mass or more.

The component (B) is a polyglycerol fatty acid ester obtained by esterifying polyglycerol in which primary hydroxyls among all hydroxyls is 50% or more and preferably 55% or more and which has an average degree of polymerization of from 6 to 14 and preferably from 6 to 12 calculated from hydroxyl value, and fatty acid having the number of carbon atoms of 12 or more, preferably 14 and further preferably 18 or more. From the viewpoint of solubility into component (A), the HLB of component (B) is less than 13.5, 12.5 or less, and more preferably 12.0 or less. The lower limit can be 7.0 or more, 8.0 or more, 9.0 or more, 9.5 or more, 10.0 or more, and the like. The proportion of the primary hydroxyl in the present specification is measured using method of measuring nuclear magnetic resonance spectrum (NMR) against carbon atoms. In addition, the hydroxyl value can be measured by the method known in the art. Incidentally, nuclear magnetic resonance spectrum (NMR) against carbon atoms can be measured as follows. Five hundred milligrams of polyglycerol are dissolved in 2.8 ml of heavy water, and after filtration, $^{13}$CNMR (125 MHz) spectrum is obtained by gated decoupling. According to the gated decoupled measurement method, the peak intensity is proportional to the number of carbon atoms. In the $^{13}$C chemical shift showing the presence of primary hydroxyl and secondary hydroxyl, methylene carbon ($CH_2OH$) is present near 63 ppm and methyne carbon (CHOH) is present near 71 ppm, and the presence ratio of primary hydroxyl to secondary hydroxyl is calculated by analysis of signal intensity of each of the two kinds. However, the methyne carbon showing the secondary hydroxyl overlaps with the methylene carbon peak which is further adjacent to the methyne carbon binding to the methylene carbon showing primary hydroxyl, and integral value of itself cannot be obtained, so that the integral value is calculated by the signal intensity near 74 ppm of methylene carbon adjacent to the methyne carbon.

The component (B) includes, for example, polyglyceryl-10 diisostearate, polyglyceryl-12 diisostearate, polyglyceryl-14 diisostearate, polyglyceryl-10 distearate, polyglyceryl-10 dioleate, polyglyceryl-10 trioleate, polyglyceryl-10 pentaoleate, polyglyceryl-6 dioleate, polyglyceryl-10 dimyristate, polyglyceryl-10 trilaurate, polyglyceryl-6 diisostearate, and the like.

The content of component (B) in the cosmetic composition of the present invention is, from the viewpoint of washout property and usability, preferably from 3 to 40% by mass, more preferably from 6 to 35% by mass, and further preferably from 9 to 30% by mass. The content in the case where two or more kinds of component (B) are used refers to the total amount thereof.

The component (C) is one or more kinds selected from the group consisting of polyglycerol fatty acid ester having HLB of 13.5 or more and polyglycerol monoalkyl ether having HLB of 12 or more. Among them, polyglycerol fatty acid ester using polyglycerol in which primary hydroxyls among all hydroxyls is 50% or more is preferable.

The component (C) includes, for example, polyglyceryl-10 isostearate, polyglyceryl-12 isostearate, polyglyceryl-14 isostearate, polyglyceryl-10 stearate, polyglyceryl-10 oleate, polyglyceryl-10 myristate, polyglyceryl-10 laurate, polyglyceryl-10 caprate, polyglyceryl-6 oleate, polyglyceryl-6 caprylate, polyglyceryl-5 laurate, polyglyceryl-5 oleate, polyglyceryl-20 diisostearate, polyglyceryl-4 lauryl ether, and the like.

The content of the component (C) in the cosmetic composition of the present invention is, from the viewpoint of washout property and usability, preferably from 0.5 to 30% by mass, more preferably from 1 to 25% by mass, further preferably from 1.5 to 20% by mass, and further more preferably from 2 to 15% by mass. The content in the case where two or more kinds of component (C) are used refers to the total amount thereof.

The mixed HLB of components (B) and (C) is, from the viewpoint of washout property and usability, from 11.1 to 15.0, preferably from 11.5 to 14.5, and more preferably from 11.7 to 135.

As used herein, HLB refers to value calculated by the following Griffin calculation method or organic conceptual diagram method, and the mixed HLB of components (B) and (C) is calculated by utilizing additivity. In other words, the mixed HLB used herein is a weighted average value of component (B) and component (C).

When calculating HLB of polyglycerol fatty acid ester used herein, the following formula is used.

$$HLB=20(1-S/A)$$

S: saponification value of polyglycerol fatty acid ester
A: neutralization value of raw material fatty acid The HLB of component (C), polyglycerol alkyl ether is calculated from organic conceptual diagram. Organic conceptual diagram has been proposed by A. FUJITA, and the details thereof are explained in "*Pharmaceutical Bulletin*," vol. 2, 2, pp. 163-173 (1954), "*Kagaku no Ryoiki (Journal of Japanese Chemistry)*," vol. 11, 10, pp. 719-725 (1957), "*Fragrance Journal*," vol. 50, pp. 79-82 (1981), "*Yukigainenzu—kiso to ouyou— (Organic conceptual diagram—basis and application—)* (Y. KOUDA, Sankyo Shuppan Co., Ltd., 1984) and the like. In other words, this is a method including considering all organic compounds as a derivative of methane ($CH_4$), setting a constant numerical value for the number of carbon atoms, a substituent, a substituted moiety, a ring and the like thereof, adding the numerical value to obtain an organic value and an inorganic value, and plotting the organic value on X axis and the inorganic value on Y axis.

An HLB in the organic conceptual diagram means the number of the ratio of the inorganic value (IV) to the organic value (OV) in the organic conceptual diagram multiplied by 10, i.e. "inorganic value (IV)/organic value (OV)×10."

Total content of components (B) and (C) is, from the viewpoint of washout property, preferably from 5 to 40% by mass, more preferably from 8 to 35% by mass, and further preferably from 10 to 30% by mass.

The method of calculating an average degree of polymerization of polyglycerol in components (B) and (C) is determined by hydroxyl value on the basis of the following formula. In addition, the determination method of the number of moles of polyglycerol is to calculate the molecular weight from an average degree of polymerization to calculate the number of moles.

$$OHV=56110(n+2)/(74n+18)$$

OHV: a hydroxyl value of polyglycerol
n: an average degree of polymerization of polyglycerol A polyglycerol fatty acid ester of components (B) and (C) is easily obtained by an esterification according to the conventional method of polyglycerol and fatty acid, or addition polymerization of fatty acid and glycidol. The esterification of polyglycerol and fatty acid can be carried out, but not particularly limited, for example, by heating polyglycerol and fatty acid at the range of from preferably 100° to 300° C., and more preferably from 120° to 260° C., while removing water in the presence of an acidic catalyst (phosphate, p-toluen sulfonate, and the like) or alkaline catalyst (sodium hydroxide) or without a catalyst. In addition, the reaction may be carried out in the presence of an inert gas. Thus obtained ester may be purified depending upon the purpose. The purification can utilize extraction by an organic solvent, fractionation, or chromatogram separation by a column which is loaded with synthetic absorbent or gel filtration agent, in addition to distillation technique such as distillation under reduced pressure, molecular distillation or steam distillation. Incidentally, ester exchange with polyglycerol may be carried out using an ester of fatty acid in place of fatty acid, to obtain the polyglycerol fatty acid ester of interest.

The method of producing polyglycerol monoalkyl ether of component (C) includes, but not particularly limited to, a method including adding glycidol to an aliphatic alcohol to have the specified presence molar ratio of the alcohol/glycidol in the presence of basic catalyst to carry out reaction, a method of reacting α-olefin epoxide with polyglycerol thereby to obtain polyglycerol monoalkyl ether, a method of opening the ring of alkylglycidyl ether in the presence of an acidic catalyst or alkaline catalyst using polyglycerol, and the like.

The cosmetic composition of the present invention may further contain the following component (D). The transparency in resin vessel storage under high moisture can be maintained for a long period of time by containing component (D). The component (D) is one or more kinds of nonionic surfactant having HLB of less than 13.5 selected from the group consisting of polyoxyethylene glyceryl cocoate, polyoxyethylene glyceryl caprylate/caprate, and polyglycerol fatty acid ester obtained by esterifying polyglycerol having an average degree of polymerization of from 2 to 6 calculated from the hydroxyl value and fatty acid having the number of carbon atoms of from 8 to 10. In a polyglycerol in the polyglycerol fatty acid ester, primary hydroxyls among all hydroxyls are preferably 50% or more, and more preferably 55% or more. From the viewpoint of maintaining the transparency in the resin vessel storage under high moisture for a long period of time, the HLB of the component (D) is less than 13.5, preferably 12.5 or less, and more preferably 12.0 or less. The lower limits can be 7.0 or more, 8.0 or more, 9.0 or more, 9.5 or more, 10.0 or more and the like.

The component (D) includes PEG-7 (caprylic/capric) glycerides. PEG-7 glyceryl cocoate, (caprylic/capric) PEG-6 glycerides, PEG-8 glyceryl caprylate/caprate, polyglyceryl-6 dicaprate, polyglyceryl-6 tricaprylate, polyglyceryl-2 sesquicaprylate, and the like.

The content of the component (D) in the cosmetic composition of the present invention is, from the viewpoint of maintaining the transparency in the resin vessel storage under high moisture for a long period of time, preferably from 0.01 to 2% by mass, more preferably from 0.01 to 1.5% by mass, and further preferably from 0.1 to 1.0% by mass.

The cosmetic composition of the present invention can be optionally formulated with ingredients conventionally used in cosmetics. For example, the ingredient includes water, surfactant, polyhydric alcohol, thickening agents, aqueous gelating agents, oily gelating agents, powders, antioxidants, preservatives, perfumes, colorants, chelating agents, refreshing agents, plant extracts, vitamins, neutralizing agents, moisturizing agents, anti-inflammatory agents, pH adjusting agents, amino acids, and the like.

In the cosmetic composition of the present invention, complex viscosity at angular velocity of 0.1 rad/s calculated from viscoelasticity in angular velocity dependence at 25° C. with a rheometer (ARES G-2, manufactured by TA Instruments) is preferably from 100 to 50000 mPa·s, more preferably from 200 to 30000 mPa·s, and further preferably from 300 to 10000 mPa·s.

The cosmetic composition of the present invention has a transmittance at a wavelength of 750 nm with a spectrophotometer (U-3900, manufactured by Hitachi High-Tech Corporation) of preferably 80% or more, more preferably 85% or more, and further preferably 90% or more.

The cosmetic composition of the present invention preferably contains a reverse wormlike micelle structure, from the viewpoint of transparency, washout property and usability. The reverse micelle is one of associated bodies which surfactants form in oil, and has a structure in which hydrophilic group is inwardly directed and oleophilic group is outwardly directed, and the appearance of the solution is isotropic transparent. At this time, when adjusting HLB or concentration of the surfactant, the shape of the micelle changes from a sphere to an elongate wormlike (or stick) structure. This reverse wormlike micelle winds around each other in oil, and confers viscoelasticity to the oil. It is known that when the viscoelasticity of the reverse wormlike micelle solution at angular velocity dependence is measured with a rheometer, a single Maxwell model theoretical curve is concordant with the slope at a side of low frequency. Accordingly, as used herein, the reverse wormlike micelle structure is confirmed by the fact that the slope at a low angular velocity region of storage modulus (G') and loss modulus (G") is concordant with the single Maxwell model curve by viscoelasticity measurement of angular velocity dependence at 25° C. with a rheometer (ARES G-2, manufactured by TA Instruments).

The method of producing the cosmetic composition of the present invention is not particularly limited, and the cosmetic composition can be produced by the conventional method. In other words, the method includes, for example, a method including heating all ingredients at 70° C. or so and dissolving the ingredients, and stirring and cooling the ingredients near the room temperature, and the like. However, the method is not limited to this production method.

Since the cosmetic composition of the present invention has excellent washout property, has appropriate viscosity in the case where the composition is made as oily cosmetics, and has excellent usability such as good compatibility with makeup, the composition can be suitably used in oily cosmetics in particular. In addition, the cosmetic composition of the present invention experiences a phase transition to O/W emulsion by adding water as mentioned above. Since this O/W emulsion is an emulsion having excellent stability and having a fine particle size, the cosmetic composition of the present invention can be used in cosmetics such as emulsified cosmetics other than oily cosmetics. In other words, the present invention also provides cosmetics containing the cosmetic composition of the present invention. The cosmetics includes oily cleansing cosmetics, emulsified-type cleansing cosmetics, gel-formed cleansing cosmetics, a skin toner, an emulsion, a cream, a beauty serum, emulsified-type sun block cosmetics, massage oil, emollient oil, body oil, hair oil or nail oil, and the like.

The above O/W emulsion contains component (A) in an amount of from 5 to 70% by mass, component (B) in an amount of from 0.6 to 12% by mass, component (C) in an amount of from 0.5 to 12% by mass, component (D) in amount of from 0.01 to 2% by mass, and water in an amount of from 15 to 95% by mass, and the O/W emulsion having a particle size of preferably from 0.1 to 10 μm, and more preferably from 0.2 to 5 n and the like are exemplified, which can be suitably used in emulsified cosmetics and the like.

As the cosmetics of the present invention, the cosmetic composition of the present invention can be directly used, and ingredients conventionally used in the cosmetics can be properly formulated depending upon the application or purpose, in addition to the cosmetic composition of the present invention. The ingredients conventionally used in the cosmetics are as mentioned above.

The method of producing cosmetics of the present invention includes a method of producing including the step of containing each of the above ingredients. In addition, the present invention discloses a method of emulsifying cosmetics including the step of containing each of the above ingredients. Here, "step of containing each of the above ingredients" includes an embodiment of adding the previously prepared cosmetic composition of the present invention, and additionally an embodiment of separately formulating and preparing each of the above ingredients in the cosmetics. Incidentally, details of the kinds, contents, ratio or the like of the each ingredient are same as mentioned above.

EXAMPLES

The present invention will be particularly described by showing Examples, without intending to limit the scope of the present invention to the following Examples. Incidentally, all of the ingredients amounts in the Tables are "% by mass." In addition, "%" means "% by mass," unless particularly described otherwise.

<Preparation of Cosmetic Composition>

Examples 1 to 46 and Comparative Examples 1 to 11

Each of ingredients in the constituent described in Tables 1 to 6 were weighed into a glass beaker, the ingredients are heated to about 80° C. and mixed, and the mixture was stirred and cooled to near room temperature, to prepare a cosmetic composition.

The details of ingredients used in Tables 1 to 6 are shown below. Incidentally, polyglycerol fatty acid ester used in Examples was obtained by esterifying a polyglycerol and a fatty acid according to a general synthetic method.

PEG-20 glyceryl triisostearate: EMALEX GWIS-320, manufactured by Nihon Emulsion Co., Ltd.

Mineral oil: MORESCOWHITE P-70, manufactured by MORESCO Corporation, average molecular weight: 323

Ethylhexyl palmitate: SALACOS P-8 (Nisshin Oillio Group, Ltd., average molecular weight: 368.6)
Cetyl ethylhexanoate: EXCEPARL HO, manufactured by Kao Corporation, average molecular weight: 368.6
Glyceryl tri(caprylate/caprate): SUNOIL MCT-7, manufactured by Taiyo Kagaku Co., Ltd., average molecular weight: 464.6
Mineral oil 2: MORESCOWHITE P260, manufactured by MORESCO Corporation, average molecular weight: 453
Squalane: PHYTOSQUALAN, manufactured by SOPHIM, average molecular weight: 423
Octyldodecyl myristate: EXCEPARL ODM, manufactured by Kao Corporation, average molecular weight: 508.9
Ethylhexyl stearate: EXCEPARL EH-S, manufactured by Kao Corporation, average molecular weight: 397

<Transparency>

Samples were placed into a quartz cell (plastic cell), component (A) was used as a control sample, and transmittance of the component at wavelength of 750 nm (% T) was measured with a spectrophotometer (Hitachi High-Tech Corporation, U-3900). Transparency of the cosmetic compositions of each Examples and Comparative Examples were assessed according to the following criteria. The results are shown in Tables 1 to 6.

(Assessment Criteria)
⊚: 95% T or more
○: 90% T or more and less than 95% T
Δ: 80% T or more and less than 90% T
X: less than 80% T or separation <Viscosity>

Samples were subjected to a measurement of viscoelasticity of angular velocity dependence at 25° C. with a rheometer (ARES G-2, manufactured by TA Instruments), and a complex viscosity at 0.1 rad/s of angular velocity was calculated to provide a viscosity. The results are shown in Tables 1 to 6.

<Usability>

Each sample in an amount of 2 g was applied and spread to faces of 10 professional panelists who used a makeup product on a face, and the face was gently massaged for one minute or so. Usability of cosmetic compositions of each Examples and Comparative Examples was assessed according to the following criteria. The results are shown in Tables 1 to 6.

(Assessment Criteria)
⊚: Not drip off, and professional panelists who felt that compatibility with makeup was good were 8/10 or more
○: Not drip off, and professional panelists who felt that compatibility with makeup was good were from 5/10 to 7/10
Δ: Not drip off, and professional panelists who felt that compatibility with makeup was good were from 1/10 to 4/10
X: Not flow out, and no professional panelists felt that compatibility with makeup was good <Washout Property>

The condition when 1 g of sample was diluted into 100 mL of tap water was confirmed, and washout properties of cosmetic compositions of each Example and Comparative Example were assessed according to the following criteria. The results are shown in Tables 1 to 6. Incidentally, a solution in which cosmetic composition of Example 1 was diluted under the above condition was measured at room temperature with a laser diffraction particle size analyzer (LS 13 320, manufactured by BECKMAN COULTER INC.), and as a result the particle size was 0.3 sm.

(Assessment Criteria)
⊚: Evenly dispersed, and the solution becomes bluish milk white solution
○: Evenly dispersed, and the solution becomes milk white solution
Δ: The sample becomes a gel form, and takes time to be evenly dispersed
X: The sample disadvantageously floats, and is not evenly dispersed The cosmetic composition of Example 1 was subjected to a measurement of viscoelasticity of angular velocity dependence at 25° C. with a rheometer (ARES G-2, manufactured by TA Instruments) as mentioned above. The results are shown in FIG. 1. As shown in FIG. 1, since the slopes in low angular velocity region of storage modulus (G') and loss modulus (G") are concordant with single Maxwell model curve, it is found that the cosmetic composition of Example 1 has a reverse wormlike micelle structure.

TABLE 1

| | | HLB | primary OH (50% or more) | Ex. 1 | Ex. 2 | Ex. 3 | Ex. 4 | Ex. 5 | Ex. 6 | Ex. 7 | Ex. 8 | Ex. 9 | Ex. 10 |
|---|---|---|---|---|---|---|---|---|---|---|---|---|---|
| (A) | mineral oil | | | 80.0 | 80.0 | 80.0 | 80.0 | 0 | 0 | 0 | 80.0 | 80.0 | 80.0 |
| | ethylhexyl palmitate | | | 0 | 0 | 0 | 0 | 80.0 | 80.0 | 80.0 | 0 | 0 | 0 |
| | cetyl ethylhexanoate | | | 0 | 0 | 0 | 0 | 0 | 0 | 0 | 0 | 0 | 0 |
| | glyceryl tri(caprylate/caprate) | | | 0 | 0 | 0 | 0 | 0 | 0 | 0 | 0 | 0 | 0 |
| (B) | polyglyceryl-10 diisostearate | 11.1 | ○ | 15.0 | 0 | 0 | 14.0 | 0 | 0 | 0 | 0 | 0 | 0 |
| | polyglyceryl-12 diisostearate | 11.9 | ○ | 0 | 15.0 | 0 | 0 | 0 | 0 | 0 | 0 | 0 | 0 |
| | polyglyceryl-14 diisostearate | 13.3 | ○ | 0 | 0 | 15.0 | 0 | 0 | 0 | 0 | 0 | 0 | 0 |
| | polyglyceryl-10 distearate | 11.9 | ○ | 0 | 0 | 0 | 15.0 | 0 | 0 | 0 | 0 | 0 | 0 |
| | polyglyceryl-10 dioleate | 11.1 | ○ | 0 | 0 | 0 | 0 | 15.0 | 0 | 0 | 0 | 0 | 0 |
| | polyglyceryl-10 trioleate | 10.8 | ○ | 0 | 0 | 0 | 0 | 0 | 15.0 | 0 | 0 | 0 | 0 |

TABLE 1-continued

| | | HLB | primary OH (50% or more) | Ex. 1 | Ex. 2 | Ex. 3 | Ex. 4 | Ex. 5 | Ex. 6 | Ex. 7 | Ex. 8 | Ex. 9 | Ex. 10 |
|---|---|---|---|---|---|---|---|---|---|---|---|---|---|
| | polyglyceryl-6 dioleate | 9.9 | ○ | 0 | 0 | 0 | 0 | 0 | 0 | 0 | 15.0 | 0 | 0 |
| | polyglyceryl-10 dimyristate | 12.3 | ○ | 0 | 0 | 0 | 0 | 0 | 0 | 0 | 0 | 18.0 | 0 |
| | polyglyceryl-10 trilaurate | 10.4 | ○ | 0 | 0 | 0 | 0 | 0 | 0 | 0 | 0 | 0 | 16.0 |
| | polyglyceryl-6 diisostearate | 10.7 | ○ | 0 | 0 | 0 | 0 | 0 | 0 | 0 | 0 | 0 | 15.0 |
| (C) | polyglyceryl-10 isostearate | 14.9 | ○ | 5.0 | 5.0 | 5.0 | 5.0 | 0 | 0 | 0 | 2.0 | 4.0 | 5.0 |
| | polyglyceryl-10 isostearate | 13.8 | X | 0 | 0 | 0 | 0 | 0 | 0 | 0 | 0 | 0 | 0 |
| | polyglyceryl-12 isostearate | 14.9 | ○ | 0 | 0 | 0 | 0 | 0 | 0 | 0 | 0 | 0 | 0 |
| | polyglyceryl-12 isostearate | 14.3 | X | 0 | 0 | 0 | 0 | 0 | 0 | 0 | 0 | 0 | 0 |
| | polyglyceryl-14 isostearate | 17.3 | ○ | 0 | 0 | 0 | 0 | 0 | 0 | 0 | 0 | 0 | 0 |
| | polyglyceryl-10 stearate | 17.5 | ○ | 0 | 0 | 0 | 0 | 0 | 0 | 0 | 0 | 0 | 0 |
| | polyglyceryl-10 oleate | 15.9 | ○ | 0 | 0 | 0 | 0 | 5.0 | 5.0 | 5.0 | 0 | 0 | 0 |
| | polyglyceryl-10 myristate | 16.7 | ○ | 0 | 0 | 0 | 0 | 0 | 0 | 0 | 0 | 0 | 0 |
| | polyglyceryl-10 laurate | 17.1 | ○ | 0 | 0 | 0 | 0 | 0 | 0 | 0 | 0 | 0 | 0 |
| | polyglyceryl-10 caprate | 17.3 | ○ | 0 | 0 | 0 | 0 | 0 | 0 | 0 | 0 | 0 | 0 |
| | polyglyceryl-6 caprylate | 15.9 | ○ | 0 | 0 | 0 | 0 | 0 | 0 | 0 | 0 | 0 | 0 |
| | polyglyceryl-5 laurate | 15.8 | X | 0 | 0 | 0 | 0 | 0 | 0 | 0 | 0 | 0 | 0 |
| | polyglyceryl-5 oleate | 14.9 | X | 0 | 0 | 0 | 0 | 0 | 0 | 0 | 0 | 0 | 0 |
| | polyglyceryl-20 diisostearate | 15.9 | ○ | 0 | 0 | 0 | 0 | 0 | 0 | 0 | 0 | 0 | 0 |
| | polyglyceryl-4 lauryl ether | 12.3 | X | 0 | 0 | 0 | 0 | 0 | 0 | 0 | 0 | 0 | 0 |
| | mixed HLB of components (B) and (C) | | | 12.1 | 12.7 | 13.7 | 12.1 | 12.3 | 12.1 | 12.1 | 12.6 | 11.3 | 11.8 |
| | transparency | | | ◎ | ◎ | ◎ | Δ | ◎ | ◎ | ◎ | ○ | ○ | ◎ |
| | viscosity (mPa·s) | | | 660 | 230 | 250 | 540 | 681 | 603 | 582 | 261 | 255 | 283 |
| | usability | | | ◎ | ◎ | ◎ | ◎ | ◎ | ◎ | ◎ | ◎ | ◎ | ◎ |
| | washout property | | | ◎ | ◎ | ○ | ◎ | ◎ | ◎ | ◎ | ○ | ○ | ◎ |

TABLE 2

| | | HLB | primary OH (50% or more) | Ex. 11 | Ex. 12 | Ex. 13 | Ex. 14 | Ex. 15 | Ex. 16 | Ex. 17 | Ex. 18 | Ex. 19 | Ex. 20 |
|---|---|---|---|---|---|---|---|---|---|---|---|---|---|
| (A) | mineral oil | | | 80.0 | 80.0 | 80.0 | 80.0 | 80.0 | 80.0 | 80.0 | 80.0 | 80.0 | 80.0 |
| | ethylhexyl palmitate | | | 0 | 0 | 0 | 0 | 0 | 0 | 0 | 0 | 0 | 0 |
| | cetyl ethylhexanoate | | | 0 | 0 | 0 | 0 | 0 | 0 | 0 | 0 | 0 | 0 |
| | glyceryl tri(caprylate/caprate) | | | 0 | 0 | 0 | 0 | 0 | 0 | 0 | 0 | 0 | 0 |
| (B) | polyglyceryl-10 diisostearate | 11.1 | ○ | 15.0 | 15.0 | 15.0 | 15.0 | 15.0 | 15.0 | 15.0 | 15.0 | 15.0 | 18.0 |
| | polyglyceryl-12 diisostearate | 11.9 | ○ | 0 | 0 | 0 | 0 | 0 | 0 | 0 | 0 | 0 | 0 |
| | polyglyceryl-14 diisostearate | 13.3 | ○ | 0 | 0 | 0 | 0 | 0 | 0 | 0 | 0 | 0 | 0 |
| | polyglyceryl-10 distearate | 11.9 | ○ | 0 | 0 | 0 | 0 | 0 | 0 | 0 | 0 | 0 | 0 |
| | polyglyceryl-10 dioleate | 11.1 | ○ | 0 | 0 | 0 | 0 | 0 | 0 | 0 | 0 | 0 | 0 |
| | polyglyceryl-10 trioleate | 10.8 | ○ | 0 | 0 | 0 | 0 | 0 | 0 | 0 | 0 | 0 | 0 |

TABLE 2-continued

| | | HLB | primary OH (50% or more) | Ex. 11 | Ex. 12 | Ex. 13 | Ex. 14 | Ex. 15 | Ex. 16 | Ex. 17 | Ex. 18 | Ex. 19 | Ex. 20 |
|---|---|---|---|---|---|---|---|---|---|---|---|---|---|
| | polyglyceryl-6 dioleate | 9.9 | ○ | 0 | 0 | 0 | 0 | 0 | 0 | 0 | 0 | 0 | 0 |
| | polyglyceryl-10 dimyristate | 12.3 | ○ | 0 | 0 | 0 | 0 | 0 | 0 | 0 | 0 | 0 | 0 |
| | polyglyceryl-10 trilaurate | 10.4 | ○ | 0 | 0 | 0 | 0 | 0 | 0 | 0 | 0 | 0 | 0 |
| | polyglyceryl-6 diisostearate | 10.7 | ○ | 0 | 0 | 0 | 0 | 0 | 0 | 0 | 0 | 0 | 0 |
| (C) | polyglyceryl-10 isostearate | 14.9 | ○ | 0 | 0 | 0 | 0 | 0 | 0 | 0 | 0 | 0 | 0 |
| | polyglyceryl-10 isostearate | 13.8 | X | 5.0 | 0 | 0 | 0 | 0 | 0 | 0 | 0 | 0 | 0 |
| | polyglyceryl-12 isostearate | 14.9 | ○ | 0 | 5.0 | 0 | 0 | 0 | 0 | 0 | 0 | 0 | 0 |
| | polyglyceryl-12 isostearate | 14.3 | X | 0 | 0 | 5.0 | 0 | 0 | 0 | 0 | 0 | 0 | 0 |
| | polyglyceryl-14 isostearate | 17.3 | ○ | 0 | 0 | 0 | 5.0 | 0 | 0 | 0 | 0 | 0 | 0 |
| | polyglyceryl-10 stearate | 17.5 | ○ | 0 | 0 | 0 | 0 | 5.0 | 0 | 0 | 0 | 0 | 0 |
| | polyglyceryl-10 oleate | 15.9 | ○ | 0 | 0 | 0 | 0 | 0 | 5.0 | 0 | 0 | 0 | 0 |
| | polyglyceryl-10 myristate | 16.7 | ○ | 0 | 0 | 0 | 0 | 0 | 0 | 5.0 | 0 | 0 | 0 |
| | polyglyceryl-10 laurate | 17.1 | ○ | 0 | 0 | 0 | 0 | 0 | 0 | 0 | 5.0 | 0 | 0 |
| | polyglyceryl-10 caprate | 17.3 | ○ | 0 | 0 | 0 | 0 | 0 | 0 | 0 | 0 | 5.0 | 0 |
| | polyglyceryl-6 caprylate | 15.9 | ○ | 0 | 0 | 0 | 0 | 0 | 0 | 0 | 0 | 0 | 2.0 |
| | polyglyceryl-5 laurate | 15.8 | X | 0 | 0 | 0 | 0 | 0 | 0 | 0 | 0 | 0 | 0 |
| | polyglyceryl-5 oleate | 14.9 | X | 0 | 0 | 0 | 0 | 0 | 0 | 0 | 0 | 0 | 0 |
| | polyglyceryl-20 diisostearate | 15.9 | ○ | 0 | 0 | 0 | 0 | 0 | 0 | 0 | 0 | 0 | 0 |
| | polyglyceryl-4 lauryl ether | 12.3 | X | 0 | 0 | 0 | 0 | 0 | 0 | 0 | 0 | 0 | 0 |
| mixed HLB of components (B) and (C) | | | | 11.8 | 12.1 | 11.8 | 12.4 | 12.5 | 12.1 | 12.5 | 12.6 | 12.7 | 11.6 |
| transparency | | | | ◎ | ○ | ○ | ○ | ○ | ◎ | ◎ | ◎ | ◎ | ◎ |
| viscosity (mPa·s) | | | | 347 | 390 | 292 | 189 | 287 | 255 | 275 | 10000 | 580 | 180 |
| usability | | | | ◎ | ◎ | ◎ | ◎ | ◎ | ◎ | ◎ | ◎ | ◎ | ◎ |
| washout property | | | | ◎ | ◎ | ◎ | ◎ | ◎ | ◎ | ◎ | ◎ | ◎ | ◎ |

TABLE 3

| | | HLB | primary OH (50% or more) | Ex. 21 | Ex. 22 | Ex. 23 | Ex. 24 | Ex. 25 | Ex. 26 | Ex. 27 | Ex. 28 | Ex. 29 | Ex. 30 |
|---|---|---|---|---|---|---|---|---|---|---|---|---|---|
| (A) | mineral oil | | | 80.0 | 80.0 | 80.0 | 80.0 | 0 | 0 | 0 | 0 | 0 | 0 |
| | ethylhexyl palmitate | | | 0 | 0 | 0 | 0 | 0 | 0 | 0 | 0 | 0 | 0 |
| | cetyl ethylhexanoate | | | 0 | 0 | 0 | 0 | 80.0 | 80.0 | 0 | 0 | 0 | 0 |
| | glyceryl tri(caprylate/caprate) | | | 0 | 0 | 0 | 0 | 0 | 0 | 80.0 | 80.0 | 80.0 | 80.0 |
| (B) | polyglyceryl-10 diisostearate | 11.1 | ○ | 18.0 | 18.0 | 16.0 | 18.0 | 15.0 | 0 | 0 | 0 | 0 | 0 |
| | polyglyceryl-12 diisostearate | 11.9 | ○ | 0 | 0 | 0 | 0 | 0 | 0 | 0 | 0 | 0 | 0 |
| | polyglyceryl-14 diisostearate | 13.3 | ○ | 0 | 0 | 0 | 0 | 0 | 0 | 0 | 0 | 0 | 0 |
| | polyglyceryl-10 distearate | 11.9 | ○ | 0 | 0 | 0 | 0 | 0 | 0 | 0 | 0 | 0 | 0 |
| | polyglyceryl-10 dioleate | 11.1 | ○ | 0 | 0 | 0 | 0 | 0 | 15.0 | 15.0 | 18.0 | 15.0 | 15.0 |
| | polyglyceryl-10 trioleate | 10.8 | ○ | 0 | 0 | 0 | 0 | 0 | 0 | 0 | 0 | 0 | 0 |

TABLE 3-continued

|   |   | HLB | primary OH (50% or more) | Ex. 21 | Ex. 22 | Ex. 23 | Ex. 24 | Ex. 25 | Ex. 26 | Ex. 27 | Ex. 28 | Ex. 29 | Ex. 30 |
|---|---|---|---|---|---|---|---|---|---|---|---|---|---|
|   | polyglyceryl-6 dioleate | 9.9 | ○ | 0 | 0 | 0 | 0 | 0 | 0 | 0 | 0 | 0 | 0 |
|   | polyglyceryl-10 dimyristate | 12.3 | ○ | 0 | 0 | 0 | 0 | 0 | 0 | 0 | 0 | 0 | 0 |
|   | polyglyceryl-10 trilaurate | 10.4 | ○ | 0 | 0 | 0 | 0 | 0 | 0 | 0 | 0 | 0 | 0 |
|   | polyglyceryl-6 diisostearate | 10.7 | ○ | 0 | 0 | 0 | 0 | 0 | 0 | 0 | 0 | 0 | 0 |
| (C) | polyglyceryl-10 isostearate | 14.9 | ○ | 0 | 0 | 0 | 0 | 5.0 | 0 | 0 | 0 | 0 | 0 |
|   | polyglyceryl-10 isostearate | 13.8 | X | 0 | 0 | 0 | 0 | 0 | 0 | 5.0 | 0 | 0 | 0 |
|   | polyglyceryl-12 isostearate | 14.9 | ○ | 0 | 0 | 0 | 0 | 0 | 0 | 0 | 0 | 0 | 0 |
|   | polyglyceryl-12 isostearate | 14.3 | X | 0 | 0 | 0 | 0 | 0 | 0 | 0 | 0 | 0 | 0 |
|   | polyglyceryl-14 isostearate | 17.3 | ○ | 0 | 0 | 0 | 0 | 0 | 0 | 0 | 0 | 0 | 0 |
|   | polyglyceryl-10 stearate | 17.5 | ○ | 0 | 0 | 0 | 0 | 0 | 0 | 0 | 2.0 | 0 | 0 |
|   | polyglyceryl-10 oleate | 15.9 | ○ | 0 | 0 | 0 | 0 | 0 | 5.0 | 0 | 0 | 5.0 | 0 |
|   | polyglyceryl-10 myristate | 16.7 | ○ | 0 | 0 | 0 | 0 | 0 | 0 | 0 | 0 | 0 | 5.0 |
|   | polyglyceryl-10 laurate | 17.1 | ○ | 0 | 0 | 0 | 0 | 0 | 0 | 0 | 0 | 0 | 0 |
|   | polyglyceryl-10 caprate | 17.3 | ○ | 0 | 0 | 0 | 0 | 0 | 0 | 0 | 0 | 0 | 0 |
|   | polyglyceryl-6 caprylate | 15.9 | ○ | 0 | 0 | 0 | 0 | 0 | 0 | 0 | 0 | 0 | 0 |
|   | polyglyceryl-5 laurate | 15.8 | X | 2.0 | 0 | 0 | 0 | 0 | 0 | 0 | 0 | 0 | 0 |
|   | polyglyceryl-5 oleate | 14.9 | X | 0 | 2.0 | 0 | 0 | 0 | 0 | 0 | 0 | 0 | 0 |
|   | polyglyceryl-20 diisostearate | 15.9 | ○ | 0 | 0 | 4.0 | 0 | 0 | 0 | 0 | 0 | 0 | 0 |
|   | polyglyceryl-4 lauryl ether | 12.3 | X | 0 | 0 | 0 | 2.0 | 0 | 0 | 0 | 0 | 0 | 0 |
|   | mixed HLB of components (B) and (C) |   |   | 11.6 | 11.5 | 12.1 | 11.2 | 12.1 | 12.3 | 11.8 | 11.7 | 12.3 | 12.6 |
|   | transparency |   |   | ○ | ○ | ◎ | ◎ | ◎ | ◎ | ◎ | ○ | ○ | ○ |
|   | viscosity (mPa · s) |   |   | 151 | 301 | 20300 | 1440 | 500 | 668 | 766 | 510 | 351 | 564 |
|   | usability |   |   | ◎ | ◎ | ○ | ◎ | ◎ | ◎ | ◎ | ◎ | ◎ | ◎ |
|   | washout property |   |   | ◎ | ◎ | ○ | ◎ | ◎ | ◎ | ○ | ○ | ○ | ○ |

TABLE 4

|   |   | HLB | primary OH (50% or more) | Ex. 31 | Ex. 32 | Ex. 33 | Ex. 34 | Ex. 35 | Ex. 36 | Ex. 37 | Ex. 38 | Ex. 39 | Ex. 40 |
|---|---|---|---|---|---|---|---|---|---|---|---|---|---|
| (A) | mineral oil |   |   | 0 | 0 | 80.0 | 80.0 | 80.0 | 80.0 | 90.0 | 85.0 | 70.0 | 60.0 |
|   | ethylhexyl palmitate |   |   | 0 | 0 | 0 | 0 | 0 | 0 | 0 | 0 | 0 | 0 |
|   | cetyl ethylhexanoate |   |   | 0 | 0 | 0 | 0 | 0 | 0 | 0 | 0 | 0 | 0 |
|   | glyceryl tri(caprylate/caprate) |   |   | 80.0 | 80.0 | 0 | 0 | 0 | 0 | 0 | 0 | 0 | 0 |
| (B) | polyglyceryl-10 diisostearate | 11.1 | ○ | 0 | 0 | 18.00 | 10.0 | 8.0 | 8.0 | 7.5 | 11.0 | 22.5 | 28.0 |
|   | polyglyceryl-12 diisostearate | 11.9 | ○ | 0 | 0 | 0 | 0 | 0 | 0 | 0 | 0 | 0 | 0 |
|   | polyglyceryl-14 diisostearate | 13.3 | ○ | 0 | 0 | 0 | 0 | 0 | 0 | 0 | 0 | 0 | 0 |
|   | polyglyceryl-10 distearate | 11.9 | ○ | 0 | 0 | 0 | 0 | 0 | 0 | 0 | 0 | 0 | 0 |
|   | polyglyceryl-10 dioleate | 11.1 | ○ | 18.0 | 15.0 | 0 | 0 | 0 | 0 | 0 | 0 | 0 | 0 |
|   | polyglyceryl-10 trioleate | 10.8 | ○ | 0 | 0 | 0 | 0 | 0 | 0 | 0 | 0 | 0 | 0 |

TABLE 4-continued

| | | HLB | primary OH (50% or more) | Ex. 31 | Ex. 32 | Ex. 33 | Ex. 34 | Ex. 35 | Ex. 36 | Ex. 37 | Ex. 38 | Ex. 39 | Ex. 40 |
|---|---|---|---|---|---|---|---|---|---|---|---|---|---|
| | polyglyceryl-6 dioleate | 9.9 | ○ | 0 | 0 | 0 | 0 | 0 | 0 | 0 | 0 | 0 | 0 |
| | polyglyceryl-10 dimyristate | 12.3 | ○ | 0 | 0 | 0 | 0 | 0 | 0 | 0 | 0 | 0 | 0 |
| | polyglyceryl-10 trilaurate | 10.4 | ○ | 0 | 0 | 0 | 0 | 0 | 0 | 0 | 0 | 0 | 0 |
| | polyglyceryl-6 diisostearate | 10.7 | ○ | 0 | 0 | 0 | 0 | 0 | 0 | 0 | 0 | 0 | 0 |
| (C) | polyglyceryl-10 isostearate | 14.9 | ○ | 0 | 0 | 0 | 10.0 | 12.0 | 0 | 2.5 | 4.0 | 7.5 | 9.0 |
| | polyglyceryl-10 isostearate | 13.8 | X | 0 | 0 | 2.0 | 0 | 0 | 0 | 0 | 0 | 0 | 0 |
| | polyglyceryl-12 isostearate | 14.9 | ○ | 0 | 0 | 0 | 0 | 0 | 12.0 | 0 | 0 | 0 | 0 |
| | polyglyceryl-12 isostearate | 14.3 | X | 0 | 0 | 0 | 0 | 0 | 0 | 0 | 0 | 0 | 0 |
| | polyglyceryl-14 isostearate | 17.3 | ○ | 0 | 0 | 0 | 0 | 0 | 0 | 0 | 0 | 0 | 0 |
| | polyglyceryl-10 stearate | 17.5 | ○ | 0 | 0 | 0 | 0 | 0 | 0 | 0 | 0 | 0 | 0 |
| | polyglyceryl-10 oleate | 15.9 | ○ | 0 | 0 | 0 | 0 | 0 | 0 | 0 | 0 | 0 | 0 |
| | polyglyceryl-10 myristate | 16.7 | ○ | 0 | 0 | 0 | 0 | 0 | 0 | 0 | 0 | 0 | 0 |
| | polyglyceryl-10 laurate | 17.1 | ○ | 2.0 | 0 | 0 | 0 | 0 | 0 | 0 | 0 | 0 | 0 |
| | polyglyceryl-10 caprate | 17.3 | ○ | 0 | 0 | 0 | 0 | 0 | 0 | 0 | 0 | 0 | 0 |
| | polyglyceryl-6 caprylate | 15.9 | ○ | 0 | 0 | 0 | 0 | 0 | 0 | 0 | 0 | 0 | 0 |
| | polyglyceryl-5 laurate | 15.8 | X | 0 | 5.0 | 0 | 0 | 0 | 0 | 0 | 0 | 0 | 0 |
| | polyglyceryl-5 oleate | 14.9 | X | 0 | 0 | 0 | 0 | 0 | 0 | 0 | 0 | 0 | 0 |
| | polyglyceryl-20 diisostearate | 15.9 | ○ | 0 | 0 | 0 | 0 | 0 | 0 | 0 | 0 | 0 | 0 |
| | polyglyceryl-4 lauryl ether | 12.3 | X | 0 | 0 | 0 | 0 | 0 | 0 | 0 | 0 | 0 | 0 |
| mixed HLB of components (B) and (C) | | | | 11.7 | 12.1 | 11.4 | 13.0 | 13.4 | 13.4 | 12.1 | 12.1 | 12.1 | 12.0 |
| transparency | | | | ○ | ○ | ◎ | ◎ | ○ | ○ | ◎ | ◎ | ◎ | ○ |
| viscosity (mPa·s) | | | | 284 | 351 | 232 | 5900 | 16132 | 33140 | 115 | 305 | 969 | 36150 |
| usability | | | | ◎ | ◎ | ◎ | ◎ | ◎ | ◎ | ◎ | ◎ | ◎ | ○ |
| washout property | | | | ○ | ○ | ◎ | ◎ | ◎ | ○ | ○ | ◎ | ○ | ○ |

TABLE 5

| | | HLB | primary OH (50% or more) | Comp. Ex. 1 | Comp. Ex. 2 | Comp. Ex. 3 | Comp. Ex. 4 | Comp. Ex. 5 | Comp. Ex. 6 | Comp. Ex. 7 | Comp. Ex. 8 | Comp. Ex. 9 | Comp. Ex. 10 | Comp. Ex. 11 |
|---|---|---|---|---|---|---|---|---|---|---|---|---|---|---|
| (A) | mineral oil | | | 80.0 | 80.0 | 80.0 | 80.0 | 80.0 | 80.0 | 80.0 | 80.0 | 80.0 | 80.0 | 16.0 |
| | ethylhexyl palmitate | | | 0 | 0 | 0 | 0 | 0 | 0 | 0 | 0 | 0 | 0 | 57.0 |
| (B) | polyglyceryl-10 diisostearate | 11.1 | ○ | 20.0 | 0 | 0 | 0 | 0 | 0 | 0 | 4.0 | 18.0 | 15.0 | 0 |
| | polyglyceryl-10 diisostearate | 11.1 | X | 0 | 0 | 15.0 | 0 | 0 | 0 | 0 | 0 | 0 | 0 | 0 |
| | polyglyceryl-20 hexaisostearate | 11.3 | ○ | 0 | 0 | 0 | 15.0 | 0 | 0 | 0 | 0 | 0 | 0 | 0 |
| | polyglyceryl-5 dioleate | 11.9 | X | 0 | 0 | 0 | 0 | 15.0 | 0 | 0 | 0 | 0 | 0 | 0 |
| | polyglyceryl-6 dicaprylate | 10.2 | ○ | 0 | 0 | 0 | 0 | 0 | 15.0 | 0 | 0 | 0 | 0 | 0 |
| (C) | polyglyceryl-14 diisostearate | 14.3 | ○ | 0 | 0 | 0 | 0 | 0 | 0 | 15.0 | 0 | 0 | 0 | 0 |
| | PEG-20 glyceryl triisostearate | 8.0 | | 0 | 0 | 0 | 0 | 0 | 0 | 0 | 0 | 0 | 0 | 16.0 |
| (C) | polyglyceryl-10 isostearate | 16.5 | ○ | 0 | 20.0 | 5.0 | 5.0 | 5.0 | 5.0 | 5.0 | 16.0 | 0 | 0 | 0 |
| | polyglyceryl-2 caprylate | 9.5 | ○ | 0 | 0 | 0 | 0 | 0 | 0 | 0 | 0 | 0 | 2.0 | 0 |

TABLE 5-continued

|  |  | HLB | primary OH (50% or more) | Comp. Ex. 1 | Comp. Ex. 2 | Comp. Ex. 3 | Comp. Ex. 4 | Comp. Ex. 5 | Comp. Ex. 6 | Comp. Ex. 7 | Comp. Ex. 8 | Comp. Ex. 9 | Comp. Ex. 10 | Comp. Ex. 11 |
|---|---|---|---|---|---|---|---|---|---|---|---|---|---|---|
| (B) | polyglyceryl-10 isostearate | 13.2 | ○ | 0 | 0 | 0 | 0 | 0 | 0 | 0 | 0 | 0 | 5.0 | 0 |
|  | polyglyceryl-10 myristate | 16.7 | ○ | 0 | 0 | 0 | 0 | 0 | 0 | 0 | 0 | 0 | 0 | 10.0 |
|  | purified water |  |  | 0 | 0 | 0 | 0 | 0 | 0 | 0 | 0 | 0 | 0 | 1.0 |
|  | mixed HLB of components (B) and (C) |  |  | 11.1 | 16.5 | 12.5 | 12.6 | 13.1 | 11.8 | 14.9 | 15.4 | 10.9 | 11.8 | 11.3 |
|  | transparency |  |  | ◉ | separated | separated | ◉ | separated | ◉ | ◉ | separated | ○ | ◉ | ○ |
|  | viscosity (mPa·s) |  |  | 95 | not assessable | not assessable | 255 | not assessable | 78 | 68 | not assessable | 55 | 97 | 30 |
|  | usability |  |  | Δ | not assessable | not assessable | Δ | not assessable | Δ | Δ | not assessable | Δ | Δ | Δ |
|  | washout property |  |  | Δ | not assessable | not assessable | X | not assessable | ○ | Δ | not assessable | Δ | ○ | ○ |

TABLE 6

|  |  | HLB | primary OH (50% or more) | Ex. 1 | Ex. 7 | Ex. 41 | Ex. 42 | Ex. 43 | Ex. 44 | Ex. 45 | Ex. 46 |
|---|---|---|---|---|---|---|---|---|---|---|---|
| (A) | mineral oil |  |  | 80.0 | 0 | 0 | 0 | 72.0 | 0 | 0 | 0 |
|  | mineral oil 2 (average molecular weight: 453) |  |  | 0 | 0 | 0 | 0 | 8.0 | 0 | 0 | 0 |
|  | squalane (average molecular weight: 423) |  |  | 0 | 0 | 0 | 0 | 0 | 80.0 | 0 | 0 |
|  | ethylhexyl palmitate |  |  | 0 | 80.0 | 80.0 | 80.0 | 0 | 0 | 30.0 | 30.0 |
|  | cetyl ethylhexanoate |  |  | 0 | 0 | 0 | 0 | 0 | 0 | 0 | 0 |
|  | octyldodecyl myristate (average molecular weight: 508.9) |  |  | 0 | 0 | 0 | 0 | 0 | 0 | 50.0 | 0 |
|  | ethylhexyl stearate (average molecular weight: 397) |  |  | 0 | 0 | 0 | 0 | 0 | 0 | 0 | 50.0 |
|  | glyceryl tri(caprylate/caprate) |  |  | 0 | 0 | 0 | 0 | 0 | 0 | 0 | 0 |
| (B) | polyglyceryl-10 diisostearate | 11.1 | ○ | 15.0 | 0 | 0 | 0 | 15.0 | 18.0 | 0 | 0 |
|  | polyglyceryl-12 diisostearate | 11.9 | ○ | 0 | 0 | 0 | 0 | 0 | 0 | 0 | 0 |
|  | polyglyceryl-14 diisostearate | 13.3 | ○ | 0 | 0 | 0 | 0 | 0 | 0 | 0 | 0 |
|  | polyglyceryl-10 distearate | 11.9 | ○ | 0 | 0 | 0 | 0 | 0 | 0 | 0 | 0 |
|  | polyglyceryl-10 dioleate | 11.1 | ○ | 0 | 0 | 0 | 0 | 0 | 0 | 0 | 0 |
|  | polyglyceryl-10 trioleate | 10.8 | ○ | 0 | 0 | 0 | 0 | 0 | 0 | 0 | 0 |
|  | polyglyceryl-10 pentaoleate | 7.5 | ○ | 0 | 0 | 0 | 0 | 0 | 0 | 0 | 0 |
|  | polyglyceryl-6 dioleate | 9.9 | ○ | 0 | 15.0 | 14.0 | 15.0 | 0 | 0 | 15.0 | 15.0 |
|  | polyglyceryl-10 dimyristate | 12.3 | ○ | 0 | 0 | 0 | 0 | 0 | 0 | 0 | 0 |
|  | polyglyceryl-10 trilaurate | 10.4 | ○ | 0 | 0 | 0 | 0 | 0 | 0 | 0 | 0 |
|  | polyglyceryl-6 diisostearate | 10.7 | ○ | 0 | 0 | 0 | 0 | 0 | 0 | 0 | 0 |
| (C) | polyglyceryl-10 isostearate | 14.9 | ○ | 5.0 | 0 | 0 | 0 | 5.0 | 2.0 | 0 | 0 |
|  | polyglyceryl-10 isostearate | 13.8 | X | 0 | 0 | 0 | 0 | 0 | 0 | 0 | 0 |
|  | polyglyceryl-12 isostearate | 14.9 | ○ | 0 | 0 | 0 | 0 | 0 | 0 | 0 | 0 |
|  | polyglyceryl-12 isostearate | 14.3 | X | 0 | 0 | 0 | 0 | 0 | 0 | 0 | 0 |

TABLE 6-continued

| | HLB | primary OH (50% or more) | Ex. 1 | Ex. 7 | Ex. 41 | Ex. 42 | Ex. 43 | Ex. 44 | Ex. 45 | Ex. 46 |
|---|---|---|---|---|---|---|---|---|---|---|
| polyglyceryl-14 isostearate | 17.3 | ○ | 0 | 0 | 0 | 0 | 0 | 0 | 0 | 0 |
| polyglyceryl-10 stearate | 17.5 | ○ | 0 | 0 | 0 | 0 | 0 | 0 | 0 | 0 |
| polyglyceryl-10 oleate | 15.9 | ○ | 0 | 5.0 | 5.0 | 0 | 0 | 0 | 5.0 | 5.0 |
| polyglyceryl-10 myristate | 16.7 | ○ | 0 | 0 | 0 | 0 | 0 | 0 | 0 | 0 |
| polyglyceryl-10 laurate | 17.1 | ○ | 0 | 0 | 0 | 0 | 0 | 0 | 0 | 0 |
| polyglyceryl-10 caprate | 17.3 | ○ | 0 | 0 | 0 | 0 | 0 | 0 | 0 | 0 |
| polyglyceryl-6 oleate | 15.0 | ○ | 0 | 0 | 0 | 5.0 | 0 | 0 | 0 | 0 |
| polyglyceryl-6 caprylate | 15.9 | ○ | 0 | 0 | 0 | 0 | 0 | 0 | 0 | 0 |
| polyglyceryl-5 laurate | 15.8 | X | 0 | 0 | 0 | 0 | 0 | 0 | 0 | 0 |
| polyglyceryl-5 oleate | 14.9 | X | 0 | 0 | 0 | 0 | 0 | 0 | 0 | 0 |
| polyglyceryl-20 diisostearate | 15.9 | ○ | 0 | 0 | 0 | 0 | 0 | 0 | 0 | 0 |
| polyglyceryl-4 lauryl ether | 12.3 | X | 0 | 0 | 0 | 0 | 0 | 0 | 0 | 0 |
| mixed HLB of components (B) and (C) | | | 12.1 | 12.1 | 11.3 | 11.2 | 12.1 | 11.5 | 12.1 | 12.1 |
| transparency | | | ◎ | ◎ | ◎ | ◎ | ◎ | ◎ | ◎ | ◎ |
| viscosity (mPa·s) | | | 660 | 582 | 575 | 555.0 | 10050 | 40360 | 15360 | 13245 |
| usability | | | ◎ | ◎ | ◎ | ◎ | ◎ | ◎ | ◎ | ◎ |
| washout property | | | ◎ | ◎ | ◎ | ◎ | ◎ | ◎ | ◎ | ◎ |

<Storage Stability>

As to maintenance of transparency in resin vessel storage under high moisture, the cosmetic compositions of Examples 5, 34 and 47 to 48 were loaded to each of a glass vessel, a PET (polyethylene terephthalate) vessel, a PP (polypropylene) vessel, the vessels were allowed to stand in storage chamber of which moisture was set to 90% Rh or more, the appearances after one month were observed, and the appearances were visually assessed according to the following criteria.

(Assessment Criteria)
○: transparent
Δ: semi-turbid
X: white turbid and precipitation

TABLE 7

| | | HLB | primary OH (50% or more) | Ex. 34 | Ex. 5 | Ex. 47 | Ex. 48 |
|---|---|---|---|---|---|---|---|
| (A) | mineral oil | | | 80.0 | 0 | 80.0 | 0 |
| | ethylhexyl palmitate | | | 0 | 80.0 | 0 | 80.0 |
| | cetyl ethylhexanoate | | | 0 | 0 | 0 | 0 |
| | glyceryl tri(caprylate/caprate) | | | 0 | 0 | 0 | 0 |
| (B) | polyglyceryl-10 diisostearate | 11.1 | ○ | 10.0 | 0 | 9.5 | 0 |
| | polyglyceryl-12 diisostearate | 11.9 | ○ | 0 | 0 | 0 | 0 |
| | polyglyceryl-14 diisostearate | 13.3 | ○ | 0 | 0 | 0 | 0 |
| | polyglyceryl-10 distearate | 11.9 | ○ | 0 | 0 | 0 | 0 |
| | polyglyceryl-10 dioleate | 11.1 | ○ | 0 | 15.0 | 0 | 14.0 |
| | polyglyceryl-10 trioleate | 10.8 | ○ | 0 | 0 | 0 | 0 |
| | polyglyceryl-6 dioleate | 9.9 | ○ | 0 | 0 | 0 | 0 |
| | polyglyceryl-10 dimyristate | 12.3 | ○ | 0 | 0 | 0 | 0 |

TABLE 7-continued

| | | HLB | primary OH (50% or more) | Ex. 34 | Ex. 5 | Ex. 47 | Ex. 48 |
|---|---|---|---|---|---|---|---|
| | polyglyceryl-10 trilaurate | 10.4 | ○ | 0 | 0 | 0 | 0 |
| | polyglyceryl-6 diisostearate | 10.7 | ○ | 0 | 0 | 0 | 0 |
| (C) | polyglyceryl-10 isostearate | 14.9 | ○ | 10.0 | 0 | 10.0 | 0 |
| | polyglyceryl-10 isostearate | 13.8 | X | 0 | 0 | 0 | 0 |
| | polyglyceryl-12 isostearate | 14.9 | ○ | 0 | 0 | 0 | 0 |
| | polyglyceryl-12 isostearate | 14.3 | X | 0 | 0 | 0 | 0 |
| | polyglyceryl-14 isostearate | 17.3 | ○ | 0 | 0 | 0 | 0 |
| | polyglyceryl-10 stearate | 17.5 | ○ | 0 | 0 | 0 | 0 |
| | polyglyceryl-10 oleate | 15.9 | ○ | 0 | 5.0 | 0 | 5.0 |
| | polyglyceryl-10 myristate | 16.7 | ○ | 0 | 0 | 0 | 0 |
| | polyglyceryl-10 laurate | 17.1 | ○ | 0 | 0 | 0 | 0 |
| | polyglyceryl-10 caprate | 17.3 | ○ | 0 | 0 | 0 | 0 |
| | polyglyceryl-6 caprylate | 15.9 | ○ | 0 | 0 | 0 | 0 |
| | polyglyceryl-5 laurate | 15.8 | X | 0 | 0 | 0 | 0 |
| | polyglyceryl-5 oleate | 14.9 | X | 0 | 0 | 0 | 0 |
| | polyglyceryl-20 diisostearate | 15.9 | ○ | 0 | 0 | 0 | 0 |
| | polyglyceryl-4 lauryl ether | 12.3 | X | 0 | 0 | 0 | 0 |
| (D) | polyglyceryl-6 dicaprate | 10.2 | ○ | 0 | 0 | 0.5 | 1.0 |
| | mixed HLB of components (B) and (C) | | | 13.0 | 12.3 | 13.1 | 12.3 |
| | transparency | | | ◎ | ◎ | ◎ | ◎ |
| | viscosity (mPa·s) | | | 5900 | 681 | 5800 | 681 |
| | usability | | | ◎ | ◎ | ◎ | ◎ |
| | washout property | | | ◎ | ◎ | ◎ | ◎ |
| | 90% Rh or more 1M storage (Glass) | | | ○ | ○ | ○ | ○ |
| | 90% Rh or more 1M storage (PP) | | | ○ | ○ | ○ | ○ |
| | 90% Rh or more 1M storage (PET) | | | X | Δ | ○ | ○ |

TABLE 8

Formulating Example 1: Cleansing Oil A

| (Ingredient) | (% by mass) |
|---|---|
| Polyglyceryl-10 diisostearate | 12.5 |
| Polyglyceryl-10 isostearate | 7.5 |
| Polyglyceryl-2 oleate | 0.5 |
| Mineral oil | 49.5 |
| Ethylhexyl palmitate | 30 |

TABLE 9

Formulating Example 2: Cleansing Oil B

| (Ingredient) | (% by mass) |
|---|---|
| Polyglyceryl-10 dioleate | 15 |
| Polyglyceryl-10 oleate | 5 |
| Glyceryl tri(caprylate/caprate) | 80 |

TABLE 10

Formulating Example 3: Cleansing gel A

| (Ingredient) | (% by mass) |
|---|---|
| Polyglyceryl-10 diisostearate | 11 |
| Polyglyceryl-10 oleate | 9 |
| Mineral off | 50 |
| Ethylhexyl palmitate | 30 |

TABLE 11

Formulating Example 4: Bath milk

| (Ingredient) | (% by mass) |
|---|---|
| Polyglyceryl-10 diisostearate | 6 |
| Polyglyceryl-10 myristate | 2 |
| Mineral oil | 30 |
| Glycerol | 15 |
| Water | Up to 100.0 |
| Preservative/Stabilize | proper amounts |

TABLE 12

| Formulating Example 5: Nail oil | |
|---|---|
| (Ingredient) | (% by maas) |
| Polyglyceryl-10 dioleate | 5.5 |
| Polyglyceryl-10 oleate | 4.5 |
| Polyglyceryl-10 decaisostearate | 5 |
| Glyceryl tri(caprylate/caprate) | Up to 100.0 |
| Macadamia nut oil | 0.1 |
| Argania spinosa kernel oil | 0.1 |
| Jojoba oil | 5 |
| Perfume | proper amounts |

TABLE 13

| Formulating Example 6: Body oil | |
|---|---|
| (Ingredient) | (% by mass) |
| Polyglyceryl-10 diisostearate | 12 |
| Polyglyceryl-10 oleate | 3 |
| Polyglyceryl-10 decaisostearate | 5 |
| Macadamia nut oil | 10 |
| Mineral off | 70 |

TABLE 14

| Formulating Example 7: Cleaning Oil C | |
|---|---|
| (Ingredient) | (% by mass) |
| Polyglyceryl-10 diisostearate | 11.5 |
| Polyglyceryl-10 isostearate | 8.0 |
| Polyglyceryl-6 dicaprate | 0.5 |
| Mineral oil | 50.0 |
| Ethylhexyl palmitate | 30.0 |

TABLE 15

| Formulating Example 8: Cleansing Oil D | |
|---|---|
| (Ingredient) | (% by mass) |
| Polyglyceryl-10 dioleate | 17.0 |
| Polyglyceryl-10 oleate | 3.0 |
| Ethylhexyl palmitate | 45.0 |
| Octyldodecyl myristate | 30.0 |
| Olive seed oil | 5.0 |

TABLE 16

| Formulating Exmple 9: Cleansing Oil B | |
|---|---|
| (Ingredient) | (% by mass) |
| Polyglyceryl-10 dioleate | 10.5 |
| Polyglyceryl-10 oleate | 4.5 |
| Ethylhexyl palmitate | 53.0 |
| Octyldodecyl myristate | 32.0 |

TABLE 17

| Formulating Example 10: Cleansing gel B | |
|---|---|
| (Ingredient) | (% by mass) |
| Polyglyceryl-10 diisostearate | 14.0 |
| Polyglyceryl-10 isostearate | 14.0 |

TABLE 17-continued

| Formulating Example 10: Cleansing gel B | |
|---|---|
| (Ingredient) | (% by mass) |
| Mineral oil | 46.0 |
| Ethylhexyl palmitate | 26.0 |

TABLE 18

| Formulating Example 11: Emulsion | |
|---|---|
| (Ingredient) | (% by mass) |
| Polyglyceryl-10 diisostearate | 2.0 |
| Polyglyceryl-10 laurate | 0.5 |
| Squalane | 10.0 |
| Glycerol | 3.0 |
| BG | 7.0 |
| Water | Up to 100.0 |
| Bentonite | 0.8 |
| Xanthan gum | 0.3 |
| Preservative/Stabilizer/pH adjusting agent | proper amounts |

TABLE 19

| Formulating Example 12: Cream | |
|---|---|
| (Ingredient) | (% by mass) |
| Polyglyceryl-10 dioleate | 3.0 |
| Polyglyceryl-10 stearate | 3.0 |
| Octyldodecyl myristate | 14.0 |
| Olive seed oil | 10.0 |
| Glycerol | 10.0 |
| Water | Up to 100.0 |
| Carbomer | 0.3 |
| Xanthan gum | 0.15 |
| Preservative/Stabilizer/ pH adjusting agent | proper amounts |

TABLE 20

| Formulating Example 13: Hair oil | |
|---|---|
| (Ingredient) | (% by mass) |
| Polyglyceryl-10 diisostearate | 2.0 |
| Polyglyceryl-10 pentaoleate | 2.0 |
| Polyglyceryl-10 oleate | 11.0 |
| Cetyl ethylhexanoate | Up to 100.0 |
| Octyldodecyl myristate | 20.0 |
| Perfume | proper amounts |

INDUSTRIAL APPLICABILITY

The cosmetic composition of the present invention can be suitably used in cosmetics.

The invention claimed is:

1. A cosmetic composition comprising the following components (A) to (C), wherein the mixed HLB of components (B) and (C) is from 11.1 to 15.0, the component (A) is one or more kinds selected from the group consisting of hydrocarbon oil, ester oil and triglyceride, the component (B) is one or more kinds selected from the group consisting of polyglyceryl-10 diisostearate, polyglyceryl-12 diisostearate, polyglyceryl-14 diisostearate, polyglyceryl-10 distearate, polyglyceryl-10 dioleate, polyglyceryl-10 trioleate, polyglyceryl-10 pentaoleate, polyglyceryl-6 dioleate, polyglyceryl-10 dimyristate, polyglyceryl-10 trilaurate and polyglyceryl-6 diisostearate, the component (C) is one or more kinds selected from the group consisting of polyglyceryl-10 isostearate, polyglyceryl-12 isostearate, polyglyceryl-14 isostearate, polyglyceryl-10 stearate, polyglyceryl-10 oleate, polyglyceryl-10 myristate, polyglyceryl-10 laurate, polyglyceryl-6 oleate, polyglyceryl-5 laurate, polyglyceryl-5 oleate, polyglyceryl-20 diisostearate and polyglyceryl-4 lauryl ether, and the content of the component (A) is from 60 to 92% by mass, the content of the component (B) is from 6 to 35% by mass, and the content of the component (C) is from 2 to 15% by mass:

component (A): oil agent;

component (B): one or more kinds selected from the group consisting of a polyglycerol fatty acid ester having HLB of less than 13.5 consisting of a polyglycerol in which primary hydroxyls among all hydroxyls are 50% or more and which has an average degree of polymerization of from 6 to 14 and a fatty acid having the number of carbon atoms of 12 or more; and component (C): one or more kinds selected from the group consisting of a polyglycerol fatty acid ester having HLB of 13.5 or more and a polyglycerol monoalkyl ether having HLB of 12 or more.

2. The cosmetic composition according to claim 1, wherein the component (A) comprises an oil agent having a weight average molecular weight of 380 or more.

3. The cosmetic composition according to claim 2, wherein the oil agent having the weight average molecular weight of 380 or more is one or more kinds selected from the group consisting of squalane, liquid isoparaffin, hydrogenated polydecene, mineral oil, olefin oligomer, isocetyl myristate, octyldodecyl myristate, hexyldecyl stearate, ethylhexyl stearate, ethylhexyl isostearate, decyl isostearate, hexyldecyl isostearate and isostearyl isostearate.

4. The cosmetic composition according to claim 1, wherein the component (C) comprises polyglycerol fatty acid ester using polyglycerol in which primary hydroxyls among all hydroxyls are 50% or more.

5. The cosmetic composition according to claim 1, wherein the total content of the components (B) and (C) is from 8 to 40% by mass.

6. The cosmetic composition according to claim 1, further comprising the following component (D):

component (D): one or more kinds of nonionic surfactants having HLB of less than 13.5 selected from the group consisting of polyoxyethylene glyceryl cocoate, polyoxyethylene glyceryl (caprylate/caprate), and polyglycerol fatty acid ester obtained by esterifying polyglycerol having average degree of polymerization of from 2 to 6 calculated from hydroxyl value and fatty acid having the number of carbon atoms of from 8 to 10.

7. The cosmetic composition according to claim 6, wherein the component (D) comprises polyglyceryl-6 dicaprate.

8. The cosmetic composition according to claim 6, wherein the content of the component (D) is from 0.01 to 2% by mass.

9. The cosmetic composition according to claim 1, wherein a complex viscosity at 0.1 rad/s of an angular velocity calculated from a viscoelasticity of an angular velocity dependence at 25° C. with a rheometer is 100 mPa·s or more.

10. The cosmetic composition according to claim 1, wherein a transmittance at 750 nm of wavelength with a spectrophotometer is 80% or more.

11. The cosmetic composition according to claim 1, wherein the composition has a reverse wormlike micelle structure.

12. Cosmetics comprising the cosmetic composition of claim 1.

13. The cosmetics according to claim 12, wherein the cosmetics are oily cleansing cosmetics, emulsified-type cleansing cosmetics, gel-formed cleansing cosmetics, a skin toner, an emulsion, a cream, a beauty serum, emulsified-type sun block cosmetics, a massage oil, an emollient oil, a body oil, a hair oil or a nail oil.

* * * * *